United States Patent
Levanon

(10) Patent No.: US 10,254,264 B2
(45) Date of Patent: Apr. 9, 2019

(54) APPARATUS AND METHOD FOR MONITORING PREPARATION OF A FOOD PRODUCT

(71) Applicant: Ido Levanon, Ramat Gan (IL)

(72) Inventor: Ido Levanon, Ramat Gan (IL)

(73) Assignee: DRAGONTAIL SYSTEMS LTD., Ramat Gan (IL)

( * ) Notice: Subject to any disclaimer, the term of this patent is extended or adjusted under 35 U.S.C. 154(b) by 0 days.

(21) Appl. No.: 15/497,289

(22) Filed: Apr. 26, 2017

(65) Prior Publication Data
US 2018/0284091 A1    Oct. 4, 2018

Related U.S. Application Data

(60) Provisional application No. 62/478,050, filed on Mar. 29, 2017.

(51) Int. Cl.
| | |
|---|---|
| G06F 11/30 | (2006.01) |
| G01N 33/02 | (2006.01) |
| G06F 16/50 | (2019.01) |
| A21D 13/41 | (2017.01) |
| G01K 13/10 | (2006.01) |
| G01N 21/88 | (2006.01) |

(Continued)

(52) U.S. Cl.
CPC ............ *G01N 33/02* (2013.01); *A21D 13/41* (2017.01); *G01K 13/00* (2013.01); *G01K 13/10* (2013.01); *G01N 21/88* (2013.01); *G06F 16/50* (2019.01); *G01K 2207/06* (2013.01); *G01N 21/25* (2013.01); *G01N 21/35* (2013.01); *G01N 2021/8472* (2013.01); *G01N 2021/8887* (2013.01)

(58) Field of Classification Search
CPC ..................................................... G01N 33/02
See application file for complete search history.

(56) References Cited

U.S. PATENT DOCUMENTS

| | | | |
|---|---|---|---|
| 2013/0302483 A1 | 11/2013 | Riefenstein | |
| 2014/0104385 A1* | 4/2014 | Wong ................. | G06Q 10/10 348/46 |

(Continued)

FOREIGN PATENT DOCUMENTS

JP       2012/252396       12/2012

OTHER PUBLICATIONS

Office Action of NZ Application No. 733184 dated Nov. 30, 2017.

(Continued)

*Primary Examiner* — Phuong Huynh
(74) *Attorney, Agent, or Firm* — Pearl Cohen Zedek Latzer Baratz LLP

(57) ABSTRACT

An apparatus and a method for monitoring preparation of a food product are disclosed. The apparatus may include an imager and a controller. The controller may be configured to execute a method having the following steps: receiving order related data; receiving an image of the food product from the imager; analyzing the received image based on pre-stored data, received from a database, in order to extract prepared product data; comparing the extracted prepared product data to the order related data; and determining a compliance of the food product with a required quality level based on comparing the extracted prepared product data to the order related data.

18 Claims, 3 Drawing Sheets

(51) Int. Cl.
*G01K 13/00* (2006.01)
*G01N 21/25* (2006.01)
*G01N 21/84* (2006.01)
*G01N 21/35* (2014.01)

(56) References Cited

U.S. PATENT DOCUMENTS

| | | |
|---|---|---|
| 2014/0119614 A1 | 5/2014 | Mochizuki et al. |
| 2014/0133704 A1 | 5/2014 | Iizaka |
| 2014/0147015 A1 | 5/2014 | Bajema |
| 2014/0236359 A1* | 8/2014 | Minvielle .............. G01N 33/02 700/275 |
| 2015/0228062 A1 | 8/2015 | Joshi et al. |

OTHER PUBLICATIONS

Elkabets, Y., Yahel Elkabets Animation—Dragon Tail Systems, [Excerpts printed while being viewed on the Internet on Dec. 3, 2018], published on Sep 10, 2013, <URL:https://www.youtube.com/watch?v=hEqFvajBAF0 >.

Tamasi, N., DragonTail Systems [Excerpts pronted while being viewed on the Internet on Dec. 6, 2018] published on Dec. 18, 2013, <URL: https://vimeo.com/82184461 >.

Australian Finance News—Camera makes pizza quality check a snap, [Excerpts printed while being viewed on the Internet on Dec. 3, 2018], published on Jan. 29, 2017, <https://www.youtube.com/watch?v=IgqFZzwvn80 >.

Dragontail Systems—The Tale of Dragontail [Excerpts printed while being viewed on the internet on Jun. 27, 2018] published on Aug. 8, 2016, <https://vimeo.com/177997138 >.

Dragontail Systems—CCSU Preview [Excerpts printed while being viewed on the Internet on Jun. 27, 2018] published on Nov. 15, 2016, <https://vimeo.com/191710409 >.

T. Brosnan and D.W. Sun, "Improving quality inspection of food products by computer vision—a review", Journal of Food Engineering, vol. 61, Issue 1, pp. 3-16.

* cited by examiner

APPARATUS AND METHOD FOR MONITORING PREPARATION OF A FOOD PRODUCT

CROSS REFERENCE TO RELATED APPLICATIONS

This application claims the benefit of U.S. Provisional Patent Application No. 62/478,050, filed on Mar. 29, 2017 and entitled "APPARATUS AND METHOD FOR QUALITY CONTROL OF A PREPARATION OF A FOOD PRODUCT", which is incorporated in its entirety herein by reference.

BACKGROUND OF THE INVENTION

Quality control of food products, even in large commercial kitchens, is done today by manual inspection of a professional (e.g., the chef). However, human inspection, even for the most experienced professionals, is subjective and may be inconsistent. Furthermore, when checking that the served dish (e.g., pizza) includes all the ordered ingredient, the human eye may be too slow and inaccurate, and may not suffice in order to timely and accurately determine that the order was properly prepared.

Furthermore, some aspects that are important to monitor and control throughout the preparation of a food product, such as, for example, the temperature, cannot be properly evaluated in real time by human inspection.

Accordingly, there is a need for a quick and accurate automated apparatus and method for monitoring preparation of a food product.

SUMMARY OF THE INVENTION

Embodiments of the invention may be related to an apparatus and a method for quality control and preparation monitoring of a food product. A food product being prepared, for example, in a restaurant or a food chain kitchen may be inspected automatically to find out if the food product was prepared according to an order given by a customer. The apparatus may include an imager and a controller. The controller may be configured to execute a method having the following steps: receiving order related data; receiving an image of the food product from the imager; analyzing the received image based on pre-stored data, received from a database, in order to extract prepared product data; comparing the extracted prepared product data to the order related data; and determining a compliance of the food product with a required quality level based on the comparison.

In some embodiments, the presorted data may include prepared product data extracted from images of food products previously inspected. In some embodiments, the order related data may include at least one of: the type of the food product, one or more ingredients that are visible on the food product and a distribution of at least one ingredient on the food product.

In some embodiments, analyzing the received image may include identifying in the extracted prepared product data at least one of: the type of the food product, one or more ingredients that are visible on a surface of the food product and distribution of at least one ingredient on the surface of the food product.

In some embodiments, the controller may further be configured to: receive a plurality of images of food products; extract prepared product data from each image; receive for each image a corresponding order related data; receive for each image a quality level; and store in the database, for each image, the extracted prepared product data together with the corresponding order related data and quality level.

In some embodiments, determining the compliance of the food product with a required quality level may include determining if the extracted prepared product data indicates that the food product has a quality above a predetermined quality level.

In some embodiments, the apparatus may further include a thermometer, and the controller may be further configured to: receive a temperature measurement of the food product; and wherein, and determine if the food product has a required quality also based on the received temperature measurement.

In some embodiments, the apparatus may further include a spectrometer, and the controller may further be configured to: receive data related to an optical spectrum of the food product from the spectrometer; and determine if the food product may have a required quality also based on the received data related to the spectrum of the food product. In some embodiments, the description of the food product further includes a degree of doneness, and the data related to the optical spectrum of the food product may be indicative of the degree of doneness. In some embodiments, the description of the food product further may include nutritive values the data related to the optical spectrum of the food product may be indicative of the nutritive values of the food product.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1A:
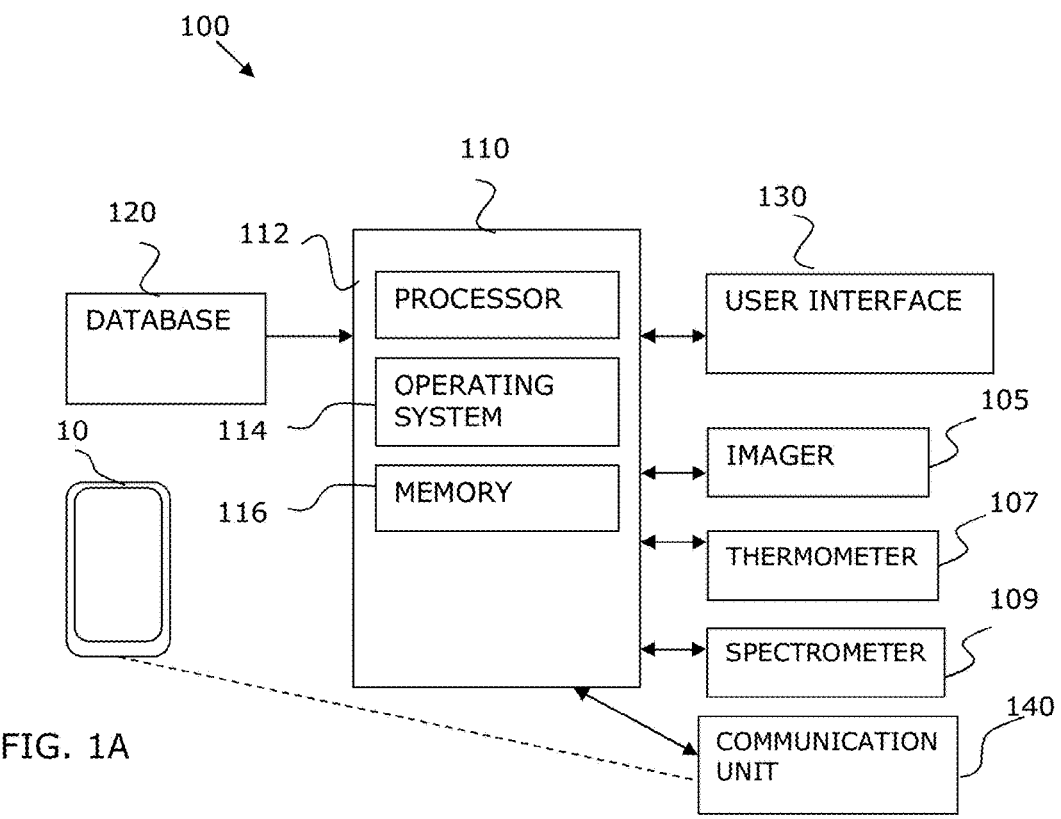
FIG. 1A is a diagrammatic representation of an apparatus for monitoring preparation of a food product according to some embodiments of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components, modules, units and/or circuits have not been described in detail so as not to obscure the invention. Some features or elements described with respect to one embodiment may be combined with features or elements described with respect to other embodiments. For the sake of clarity, discussion of same or similar features or elements may not be repeated.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Additionally, some of the described method embodiments or elements thereof can occur or be performed simultaneously, at the same point in time, or concurrently.

Embodiments of the invention may be related to an apparatus and method for monitoring preparation of a food product. A food product being prepared, for example, in a restaurant or a food chain kitchen may be inspected automatically to find out if the food product was prepared according to an order given by a customer. For example, a pizza coming out of the oven may be inspected automatically to see if the dough was baked to the right degree, the cheese was spread evenly and at the right amount and the toppings match the customer's order (e.g., ½ peperoni, ½ onion). In yet another example, an apparatus according to some embodiments of the invention may automatically inspect a hamburger dish to verify that hamburger is in the right size (e.g., 300 gr.) to the right degree of doneness, the right sauces were added and the right side dish was served therewith.

In some embodiments, the food product (e.g., pizza, hamburger, sushi, and the like) may be placed in the apparatus in order to inspect the food product preparation quality. In addition to the regular meaning of the term preparation quality, in the scope of this application "preparation quality" may refer to products' amounts, products' freshness, products' order of placement, products' color, nutritional values and temperatures. The apparatus may include an imager that is configured to take at least one image of the prepared food product. In some embodiments, the apparatus may further include additional sensors such as a thermometer, spectrometer and/or a scale. The device may further include a controller that may be configured to receive the at least one image and optionally measurements from the thermometer, spectrometer and/or the scale and to determine the quality of the food product.

Reference is now made to FIG. 1A which is a diagrammatic representation of an apparatus for monitoring preparation of a food product according to some embodiments of the invention. An apparatus 100 may include at least one imager 105, a controller 110, a database 120 and a user interface 130. Apparatus 100 may further include a communication unit 140, a thermometer 107 and/or a spectrometer 109. Apparatus 100 may be in communication with a user device 10 via communication unit 140. In some embodiments imager 105 may be the imager of user device 10. User device 10 may be a smartphone, a tablet, a laptop and the like.

In some embodiments, imager 105 may be a dedicated imager integral to apparatus 100. Imager 105 (either included in device 10 or in apparatus 100) may be any optical device, camera, etc. that is configured to capture an image and send the image to controller 110.

Thermometer 107 may be any thermometer configured to measure a temperature of the food product, for example, thermometer may include a thermocouple. Thermometer 107 may send temperature measurements of the food product to controller 110.

Spectrometer 109 may include any device that may be configured to measure properties of the food product from an optical spectrum received from the food product, for example, in an IR spectrum. The properties may include the temperature and the chemical compositions/bonds of the food product that may lead to identifying nutritive values of the food product. Spectrometer 109 may send data related to spectrographic measurements (e.g., the spectrums and/or properties) to controller 110.

Controller 110 (e.g., a server) may be or may include a processor 112 that may be, for example, a central processing unit (CPU), a chip, a cloud base computing service, or any suitable computing or computational device, an operating system 114 and a memory 116. Processor 112 may be configured to carry out methods according to embodiments of the present invention by for example executing instructions stored in a memory such as memory 116. Processor 112 may be configured to carry out methods of preparation monitoring preparation of a food product according to some embodiments of the invention.

Operating system 114 may be or may include any code segment designed and/or configured to perform tasks involving coordination, scheduling, arbitration, supervising, controlling or otherwise managing operation of controller 110, for example, scheduling execution of programs. Operating system 114 may be a commercial operating system. Memory 116 may be or may include, for example, a cloud based memory, a Random Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. Memory 116 may be or may include a plurality of memory units, which may be the same or different.

Memory 116 may store any executable code, e.g., an application, a program, a process, task or script. The executable code may include codes for preparation monitoring preparation of a food product or any other codes or instruction for executing methods according to embodiments of the present invention. The executable code may be executed by processor 112 possibly under control of operating system 114.

Database 120 may be or may include, for example, a hard disk drive, a floppy disk drive, a Compact Disk (CD) drive, a CD-Recordable (CD-R) drive, a universal serial bus (USB) device or other suitable removable and/or fixed storage unit. Additionally or alternatively, database 120 may include any cloud base storage service. Content may be stored in database 120 and may be loaded from database 120 into memory 116 where it may be processed by processor 112. For example, database 120 may include images of food products, temperature measurements, optical spectra, and extracted prepared product data together with corresponding order related data and preparation quality levels, according to embodiments of the invention.

User interface 130 may be or may include a screen, a touch screen or a pad, a mouse a keyboard and the like. User interface 130 may include audio device such as one or more speakers, earphones, a printer and/or any other suitable devices.

Communication unit 140 may be configured to communicate between controller 110 and other components of apparatus 100 (e.g., imager 105, thermometer 107, spectrometer 109 and the like) as well as with user device 10. Communication unit 140 may include a wired or wireless network interface card (NIC), a modem and the like. Furthermore, any applicable input/output (I/O) devices may be connected to controller 110 directly or via communication unit 140 or for example, a universal serial bus (USB) device or external hard drive and the like.

Figure 1B:
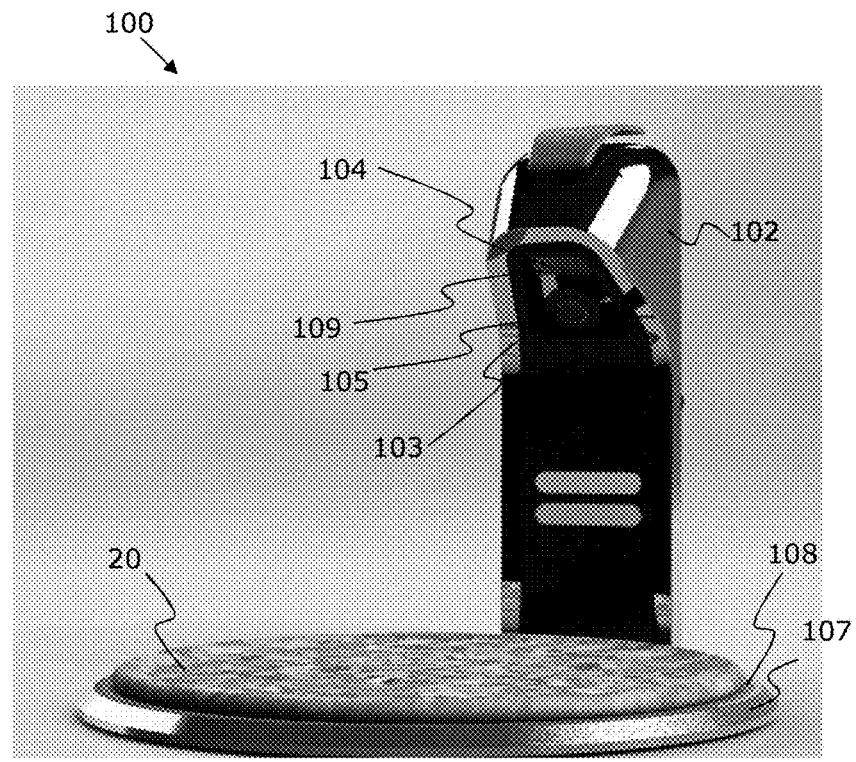
FIG. 1B is an illustration of an apparatus for monitoring preparation of the food product according to some embodiments of the invention.

Reference is now made to FIG. 1B which is an illustration of an example of an apparatus for monitoring preparation of a food product according to some embodiments of the invention. Apparatus 100 may include a housing 102 for holding at least some of the components of apparatus 100, for example, imager 105, thermometer 107 and/or spectrometer 109. Housing 102 may further be configured to receive a food product 20 (e.g., pizza) for inspection and may include a surface or a tray for receiving food product 20. In some embodiments, apparatus 100, may further include a light source 104 for illuminating the inspected food product 20. Housing 102 may further hold light source 104, such that light form light source 104 is directed towards food product 20. In some embodiments, housing 102 may hold additional components of apparatus 100, for example, communication unit 140 (not illustrated). Additionally, housing 102 may further include a holder (not illustrated) for holding user device 10. The holder may be designed to hold user device 10 such that the imager of user device 10 may be directed towards the surface of food product 20, thus allow the imager to capture images of food product 20. In some embodiments, housing 102 may further include one or more optical lenses 103 for further focusing and directing the field of view of the imager of user device 10 towards the inspected food product 20 placed on a tray 108.

Figure 2:
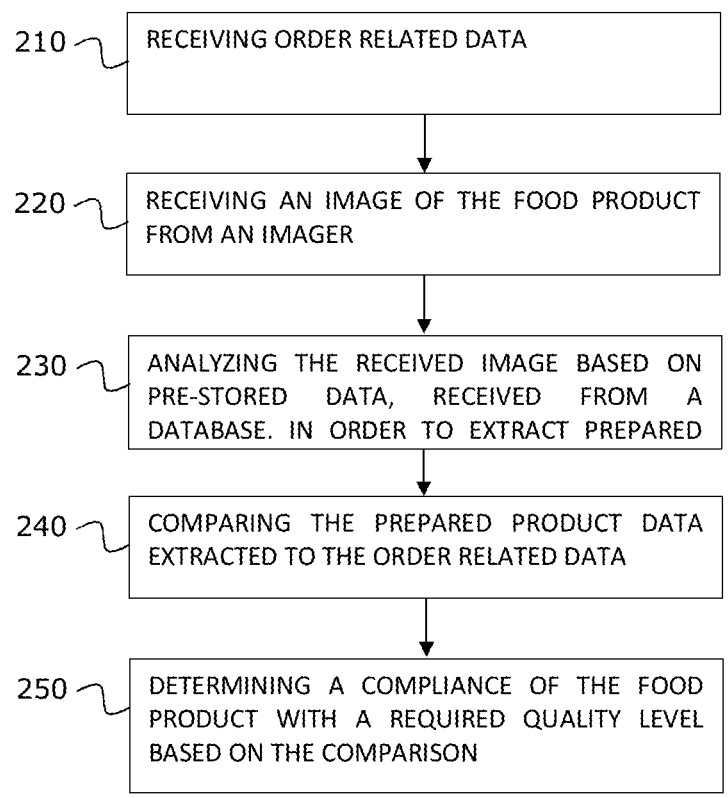
FIG. 2 is a flowchart of a method of monitoring preparation of a food product according to some embodiments of the invention.

Reference is now made to FIG. 2 which is a flowchart of a method of monitoring preparation of a food product according to some embodiments of the invention. The method of FIG. 2 may be automatically performed by processor 112 of device 100 or by any other processor. In operation 210, order related data may be received, for example, by processor 112. The order related data may include all the data that is required to prepare the food product, for example, the type of food (e.g., pizza, sushi, hamburger, etc.), ingredient that are visible on the food product (mushrooms, salmon, peperoni, double cheese, etc.,) a distribution of at least one ingredient on the food product, degree of doneness (e.g., medium, rare, well done etc.), side dishes (e.g., French fries, rise, etc.) and the like. The order related data may be received from a database of the food product provider (e.g., a restaurant), in real-time from a computer device operated by an employee of the provider, from a user device over the internet (e.g., when the user uses online food ordering service) and the like.

In operation 220, an image of the food product (e.g., food product 20) may be received from an imager (e.g., imager 105 or the imager of user device 10). The prepared food product 10 may be placed for inspection in housing 102 such that at least one imager 105 and/or the imager of user device 10 may take one or more images of food product 20.

In operation 230, the received image may be analyzed, based on pre-stored data, received from a database (e.g., database 120), in order to extract prepared product data. The image may undergo any image processing known in the art.

For example, a deep convolutional neural network algorithm (e.g., that may run on user device 10) may be used to identify food product 20 (e.g., a pizza) in one or more captured images. In another example, fully convolutional network algorithms may be applied to identify details, such as toppings, based on analysis of each pixel of the image. In yet another example, a neural style transfer algorithm may be applied to enhance the image textures and make the product image more comprehensible.

The processed image may be compared to pre-stored data that may include prepared product data extracted from images of food products previously inspected. The comparison may yield an identification of product related data. For example, the controller may compare an image processed by fully convolutional network algorithm to previously stored processed images, wherein the previously stored processed images include identification of small details that were associated with product data, such as for example, toppings, in the images done using the fully convolutional network algorithm. A method of collecting the pre-stored data is disclosed in FIG. 3. In some embodiments, the comparison may allow identifying in the extracted prepared product data at least one of: the type of the food product, one or more ingredients that are visible on a surface of the food product and distribution of at least one ingredient on the surface of the food product.

In operation 240, the extracted prepared product data may be compared to the order related data to see if the food product includes the correct type of food, has all the ordered ingredients at a sufficient amount and distribution. For example, if order product is an onion-peperoni pizza, the comparison may verify if an onion-peperoni pizza was prepared with the correct amount and distribution of onions and peperoni. In yet another example, if the order included a 200 gram hamburger with tomatoes, lettuce but with no pickles, and mash potatoes as a side dish, the comparison may verify if all required ingredient are included in the product and no additional ingredients (e.g., pickles) were mistakenly added.

In operation 250, a compliance of the food product with a required preparation quality level may be determined based on the comparison. The term "preparation quality" as used herein may include a set of preparation parameters that should be met in order for the food product to be served/delivered to the client. For example, preparation parameters may include, a temperature range in which the product is to be served, colors/textures of various ingredients (e.g., color of dough, freshness of vegetables, color of cheese, color of French Fries, etc.), the amount and distribution of various ingredients and the like. In some embodiments, if the extracted prepared product data reveals that the product was not prepared according to the order, the food product may be labeled as "not having the required quality level". However, if the extracted prepared product data reveals that the food product was correctly prepared, an additional monitoring may be done using the extracted prepared product data.

In some embodiments, the pre-stored data may include association between processed images (extracted prepared product data) to required preparation quality levels (e.g., a set of preparation parameters). Accordingly, the extracted prepared product data from the received image of the product may be compared to pre-stored extracted prepared product data to see if the product has the required quality level. In some embodiments, more than two quality levels may be determined (i.e., more levels than merely sufficient/insufficient).

In some embodiments, three quality levels may be determined, insufficient, sufficient and almost sufficient). For example, if the food product had received the insufficient quality level the product may not be served, if the food product had received the sufficient quality level, the food product may be served and if the food product had received the "almost sufficient" quality level the food product may further be inspected by a human inspector (e.g., a cook) that may determine if the food product can be served.

In some embodiments, the quality level may include assigning quality levels to different properties of the food product. For example, a quality level of a pizza may include the coverage of the cheese, the color of the dough, the coverage of the source, the amount and distribution of the toppings and the like. In some embodiments, each property may be given a quality level and the quality level of the food product may be calculated based on the quality level of each property. In some embodiments, each property may be assigned with different weight and the calculation may include giving each property quality level the assigned weight. For example, the coverage of the cheese may be given a higher weight than the distribution of the toppings.

In some embodiments, a temperature measurement of the food product may be received from a temperature sensor/thermometer (e.g., thermometer 107). In some embodiments, the compliance of the food product with a required quality level (in operation 250) may further be determined based on the temperature measurement. For example, the temperature of the pizza may be measured and compared to the required temperature for serving/delivering a pizza. If the temperature is too low (e.g., the pizza may be delivered cold) the pizza may be reheated or discarded.

In some embodiments, data related to a spectrum of the food product may be received from spectrometer 109. For example, the data related to a spectrum may include, the spectrum and/or properties extracted from the spectrum, such as temperature, chemical compositions, chemical bonds nutritive values and the like. In some embodiments, the compliance of the food product with a required quality level (in operation 250) may further be determined based on the received data related to the spectrum. The received spectrum may indicate the temperature inside the food product, thus may for example, determine a degree of doneness of a burger or a steak. In some embodiments, the spectrum may indicate the nutritive values of the food product, such as, proteins, fat, carbohydrates and more.

Figure 3:
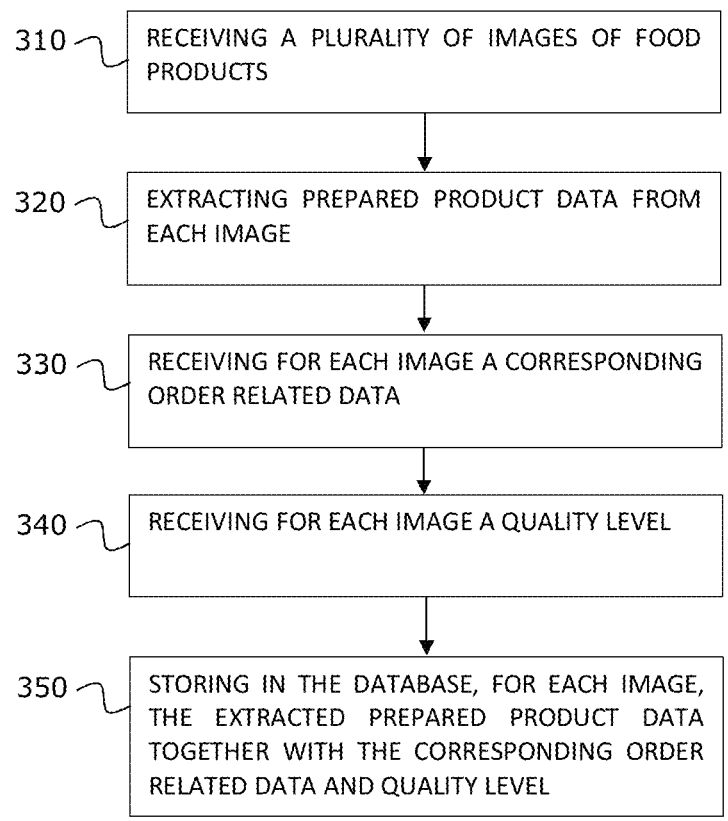
FIG. 3 is a flowchart of additional steps for collecting a pre-stored data in the method of monitoring preparation of a food product according to some embodiments of the invention.

Reference is now made to FIG. 3 which is a flowchart of additional steps for collecting pre-stored data in the method of monitoring preparation of a food product according to some embodiments of the invention. The steps of FIG. 3 may be performed by processor 102 or by any other processor. In operation 310, a plurality of images of food products may be received, for example, from an imager 105 or an imager of a user device 10. The plurality of images of food products may be taken during the preparation of a plurality of food products. For example, the plurality of images may include images of: various types of pizzas, various types of sushi, various types of pasta and the like.

In operation 320, prepared product data from each image may be extracted, for example, using the same image processing method disclosed above.

In operation 330, for each image a corresponding order related data may be received, for example, from a user device or a database.

In operation 340, for each image a quality level may be received, form a user device and/or a user interface. For example, a professional (e.g., a cook) may determine a quality level for each food product appearing in the plurality of images and may upload the determined quality level to controller 110 using a user device or a user interface.

In operation 350, for each image, the extracted prepared product data together with the corresponding order related data and quality level may be stored in a database (e.g., database 120). Database 120 may include lookup tables of extracted prepared product data associated with order related data and a quality level. For example, the lookup table may include data extracted from an image of a prepared pizza peperoni, with the order related data of "pizza" +"peperoni" and the quality level given to this pizza (e.g., insufficient). The lookup table may include data extracted from an image of an additional prepared pizza peperoni, with the order related data of "pizza"+"peperoni" and the quality level given to the additional pizza (e.g., sufficient). Accordingly, data extracted from an image of pizza peperoni in operation 230, may be compared to the extracted data stored in database to see if the prepared peperoni pizza has a sufficient quality level.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. An apparatus for monitoring preparation of a food product, comprising:
   at least one imager; and
   a controller configured to:
      receive order related data comprising one or more ingredients that are visible on the food product and a distribution of at least one ingredient on the food product;
      receive an image of the food product from the at least one imager;
      process the received image to identify details in the image;
      compare the processed image to pre-stored data, received from a database, in order to extract prepared product data;
      identify in the extracted prepared product data the one or more ingredients that are visible on the food product and the distribution of at least one ingredient on the food product;
      compare the extracted prepared product data to the order related data;
      and
      determine a compliance of the food product with a required quality level based on comparing the extracted prepared product data to the order related data,
   wherein the pre-stored data comprises processed images comprising identified one or more ingredients that are visible on the food product and the distribution of at least one ingredient on the food product related to food products, previously inspected.

2. The apparatus of claim 1, wherein processing the received image comprises analyzing pixels of the image.

3. The apparatus of claim 1, wherein the order related data includes the type of the food product.

4. The apparatus of claim 1, wherein the controller is further configured to:
receive a plurality of images of food products;
extract prepared product data from each image;
receive for each image a corresponding order related data;
receive for each image a quality level; and
store in the database, for each image, the extracted prepared product data together with the corresponding order related data and quality level.

5. The apparatus of claim 1, wherein determining the compliance of the food product with a required quality level comprises determining if the extracted prepared product data indicates that the food product has a quality above a predetermined quality level.

6. The apparatus according to claim 1, further comprising a temperature sensor, and wherein the controller is further configured to:
receive a temperature measurement of the food product from the temperature sensor; and
determine if the food product has a required quality also based on the received temperature measurement.

7. The apparatus according to claim 1, further comprising a spectrometer, and wherein the controller is further configured to:
receive data related to an optical spectrum of the food product from the spectrometer; and
determine if the food product has a required quality also based on the received data related to the optical spectrum of the food product.

8. The apparatus of claim 7, wherein the description of the food product further comprises a degree of doneness,
and wherein the data related to the optical spectrum of the food product is indicative of the degree of doneness.

9. A computer implemented method of monitoring preparation of food products comprising:
receiving order related data comprising one or more ingredients that are visible on the food product and a distribution of at least one ingredient on the food product;
receiving an image of the food product from an imager;
processing the received image to identify details in the image;
comparing the processed image to pre-stored data, received from a database, in order to extract prepared product data;
identifying in the extracted prepared product data the one or more ingredients that are visible on the food product and the distribution of at least one ingredient on the food product;
comparing the extracted prepared product data to the order related data; and
determining a compliance of the food product with a required quality level based on comparing the extracted prepared product data to the order related data,
wherein the pre-stored data comprises processed images comprising identified one or more ingredients that are visible on the food product and the distribution of at least one ingredient on the food product related to food products, previously inspected.

10. The computer implemented method of claim 9, wherein processing the received image comprises analyzing pixels of the image.

11. The computer implemented method of claim 9, wherein the order related data includes the type of the food product.

12. The computer implemented method of claim 9, further comprising:
receiving a plurality of images of food products;
extracting prepared product data from each image;
receiving for each image a corresponding order related data;
receiving for each image a quality level; and
storing in the database, for each image, the extracted prepared product data together with the corresponding order related data and quality level.

13. The computer implemented method of claim 9, wherein determining the compliance of the food product with a required quality level comprises determining if the extracted prepared product data indicates that the food product has a quality above a predetermined quality level.

14. The computer implemented method according to claim 9, further comprising:
receiving a temperature measurement of the food product from a thermometer; and wherein
determining if the food product has a required quality is also based on the received temperature measurement.

15. The computer implemented method according to claim 9, further comprising:
receiving a data related to an optical spectrum of the food product from a spectrometer; and wherein
determining if the food product has a required quality is also based on the received data related to the optical spectrum of the food product.

16. The computer implemented method of claim 15, wherein the description of the food product further comprises a degree of doneness,
and wherein the data related to the optical spectrum of the food product is indicative of the degree of doneness.

17. The computer implemented method of claim 15, wherein the description of the food product further comprises nutritive values,
and wherein the data related to the optical spectrum of the food product is indicative of the nutritive values of the food product.

18. The apparatus of claim 1, wherein the pre-stored data comprises identified details comprising colors that are visible on the surface of the food products.

* * * * *